United States Patent
Chen et al.

(10) Patent No.: US 10,815,221 B2
(45) Date of Patent: Oct. 27, 2020

(54) CRYSTAL FORMS OF AN ANDROGEN RECEPTOR ANTAGONIST, PREPARATION METHOD AND USE THEREOF

(71) Applicant: Crystal Pharmaceutical (Suzhou) Co., Ltd., Suzhou (CN)

(72) Inventors: Minhua Chen, Suzhou (CN); Yanfeng Zhang, Suzhou (CN); Kaiqiang Yan, Suzhou (CN); Qiyue Liu, Jiangsu (CN); Xiaoyu Zhang, Suzhou (CN); Jiaoyang Li, Suzhou (CN)

(73) Assignee: Crystal Pharmaceutical (Suzhou) Co., Ltd., Suzhou (CN)

( * ) Notice: Subject to any disclaimer, the term of this patent is extended or adjusted under 35 U.S.C. 154(b) by 16 days.

(21) Appl. No.: 16/328,249

(22) PCT Filed: Aug. 25, 2017

(86) PCT No.: PCT/CN2017/099036
§ 371 (c)(1),
(2) Date: Feb. 25, 2019

(87) PCT Pub. No.: WO2018/036558
PCT Pub. Date: Mar. 1, 2018

(65) Prior Publication Data
US 2020/0239450 A1 Jul. 30, 2020

(30) Foreign Application Priority Data

Aug. 26, 2016 (CN) ............... 2016 1 0737732
Sep. 30, 2016 (CN) ............... 2016 1 0871736
Oct. 8, 2016 (CN) ............... 2016 1 0876685

(51) Int. Cl.
C07D 403/12 (2006.01)

(52) U.S. Cl.
CPC ........ C07D 403/12 (2013.01); *C07B 2200/13* (2013.01)

(58) Field of Classification Search
None
See application file for complete search history.

(56) References Cited

U.S. PATENT DOCUMENTS 10,010,530 B2 * 7/2018 Tormakangas ..... A61K 31/4155

FOREIGN PATENT DOCUMENTS

| CN | 102596910 A | 7/2012 |
|---|---|---|
| WO | 2012143599 A1 | 10/2012 |
| WO | 2016120530 A1 | 8/2016 |
| WO | 2019028689 A1 | 2/2019 |

OTHER PUBLICATIONS

Guideline for Residual Solvents in Pharmaceuticals. Pharmaceutical Review. 1998;307:1-11.
Ogata, Operation of Chemical Experiments. Nankodo Co., Ltd. Japan. pp. 366-399, Nov. 20, 1963.
Separation and Purification. Lectures on Chemistry 2. Maruzen Co., Ltd. pp. 159-162, 184-193, Jan. 25, 1967.
Takata, API Form Screening and Selection in Drug Discovery Stage. Pharm Stage. 2007;6(10):20-25.
Yuming, Part 2—Crystallization Theory, Part 3—General Method of Crystallization, Part 4—Pharmaceutical Crystallization. Organic Compound Crystallization Handbook and Principles. pp. 17-23, 37-40, 45-51, 57-65, (2008).

* cited by examiner

*Primary Examiner* — Kamal A Saeed
(74) *Attorney, Agent, or Firm* — McCarter & English, LLP; Steven G. Davis; Wei Song

(57) ABSTRACT

The present disclosure relates to novel crystalline forms of an androgen receptor antagonist drug (ODM-201 represented by formula (I)), preparation method thereof and use thereof. The crystalline form B or the crystalline form C of ODM-201 provided by the present disclosure has low hygroscopicity, good stability, high solubility, excellent flowability, optimal particle size with uniform distribution, which provides a new choice for the preparation of drugs containing ODM-201 and is of great value for drug development.

Formula (I)

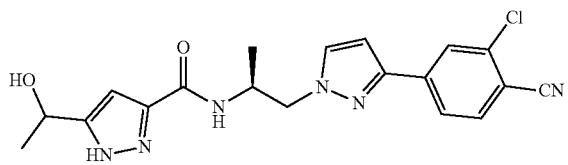

14 Claims, 11 Drawing Sheets

CRYSTAL FORMS OF AN ANDROGEN RECEPTOR ANTAGONIST, PREPARATION METHOD AND USE THEREOF

TECHNICAL FIELD

The present disclosure relates to the field of pharmaceutical crystal technology, particularly relates to novel crystalline forms of an androgen receptor antagonist drug, processes for preparation and use thereof.

BACKGROUND

Prostate cancer has become an important disease threatening male's health. Its incidence rate is higher in western countries and shows a year-by-year upward trend. The growth of the number of prostate cancer patients in recent years is accelerated in the Asian countries with lower morbidity rate in the past. Commonly used methods for clinical treatment of prostate cancer are surgical resection, radiation therapy and blocking androgen endocrine therapy. Androgen is closely related to the growth of prostate and the occurrence of prostate cancer. Therefore, endocrine therapy has become an effective way for treating prostate cancer. Endocrine therapy includes orchiectomy, estrogen therapy, gonadotropin releasing hormone analog therapy, gonadotropin releasing hormone antagonist therapy, androgen antagonist therapy, etc., wherein, androgen antagonist therapy is one of the primary methods for clinical treatment of prostate cancer, which can be used to treat early-stage prostate cancer alone or serve as adjuvant therapy with surgery. Androgen receptors, as targets for the biological effects of androgens, play an important role in the field of biomedical research.

Clinical trials have shown that exogenous androgen in patients with prostate cancer can lead to aggravation of the patient's condition; on the contrary, if the testicles are removed and the level of androgens in the patient is reduced, the condition is relieved, indicating that androgen plays an important role in the development of prostate cancer. According to the receptor theory, androgen must bind with androgen receptor (AR) to cause subsequent physiological and pathological effects, which is the basis for the application of androgen receptor (AR) antagonist in the treatment of prostate cancer. In vitro experiments have demonstrated that AR antagonists can inhibit prostate cell proliferation and promote apoptosis. Depending on the chemical structure of the AR antagonist, it can be classified into steroidal AR antagonists and non-steroidal AR antagonists. Non-steroidal drugs have better anti-androgenic activity and do not have hormone-like side effects of steroids, so they are more suitable for the treatment of prostate cancer.

ODM-201 (BAY-1841788) is a non-steroidal oral androgen receptor (AR) antagonist used clinically to treat prostate cancer. The binding affinity of ODM-201 to AR is high, with Ki=11 nM and IC50=26 nM. Ki is the dissociation constant between ODM-201 and AR complex. The smaller the value, the stronger the affinity is. IC50 (half maximal inhibitory concentration) refers to the measured semi-inhibitory concentration, which represents the concentration of a drug that is required for 50% inhibition in vitro, and the lower the value, the stronger the inhibitory ability of the drug is. In addition, ODM-201 does not cross the blood-brain barrier, thus can reduce neurological side effects such as epilepsy. Bayer has confirmed the efficacy and safety of ODM-201 in clinical trials, demonstrating its potential for the treatment of prostate cancer.

The chemical name of ODM-201 is N—((S)-1-(3-(3-chloro-4-cyanophenyl)-1H-pyrazol-1-yl)-propan-2-yl)-3-(1-hydroxyethyl-1H-pyrazole-5-carboxamide. It is known to those skilled in the art that this chemical name indicates the tautomer: N—((S)-1-(3-(3-chloro-4-cyanophenyl)-1H-pyrazol-1-yl)-propan-2-yl)-5-(1-hydroxyethyl)-1H-pyrazole-3-carboxamide, CAS number: 12975 38-32-9, and the structure is shown as follows:

Formula (I)

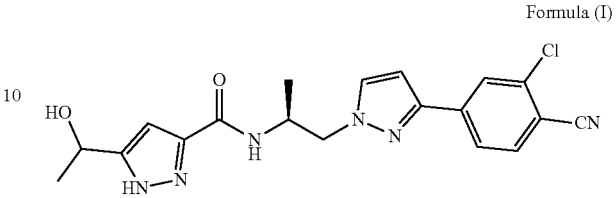

Different crystalline forms of solid chemical drugs can lead to differences in their solubility, stability, flowability and compressibility, thereby affecting the safety and efficacy of pharmaceutical products containing the compounds (see K. Knapman, *Modern Drug Discovery*, 3, 53-54, 57, 2000.), which resulting in differences in clinical efficacy. The discovery of new crystalline forms (including anhydrates, hydrates, solvates, etc.) of the active pharmaceutical ingredients may provide drug substance with processing advantages and better physical and chemical properties such as better bioavailability, better storage stability, easiness to process, and easiness to purify. Some novel crystalline forms may serve as intermediate crystal forms to facilitate solid state transformation to desired forms. Novel polymorphs of raw materials can enhance the performance of the drug and provide more solid states in the formulation.

Patent CN102596910B discloses the preparation of ODM-201, but does not disclose any crystalline form information. WO2016120530A1 discloses a crystalline form I of ODM-201 represented by formula (I) (CAS number: 1297538-32-9), a crystalline form I' of ODM-201 represented by formula (Ia) (CAS number: 1976022-48-6) and a crystalline form I" of ODM-201 represented by formula (Ib) (CAS number: 1976022-49-7). *Expert Rev. Anticancer Ther.* 15 (9), (2015) reported that ODM-201 represented by formula (I) is composed of diastereomers (Ia) and (Ib) with a ratio of 1:1. Only crystalline form I of ODM-201 was reported.

(Ia)

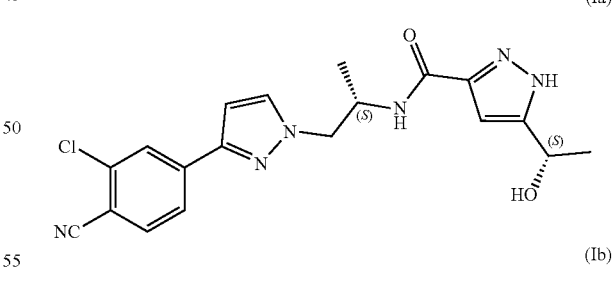

(Ib)

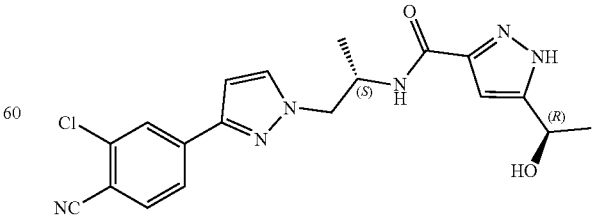

However, crystalline form I has low solubility and high hygroscopicity, and the preparation of crystalline form I requires the use of a highly toxic acetonitrile solvent. Acetonitrile is animal carcinogenic and is class 2 solvent that should be controlled during the process development stage. The preparation method of the crystalline form I is relatively complicated. The preparation cycle is long and heating is required in the process. Thus the industrial preparation cost is increased, which is disadvantageous for industrial production. In order to overcome the above drawbacks, there is still a need in the art to systematically develop other crystalline forms of ODM-201 of formula (I), to simplify the preparation process, to realize pharmacological development and release potential, and to promote the preparation of a better formulation containing the active pharmaceutical ingredient.

The inventors discovered crystalline form B and crystalline form C of the present disclosure through experiments, and found that the crystalline form B and crystalline form C of the present disclosure have more excellent properties than the prior art. Dissolution is a prerequisite for drug absorption, and increased solubility will help to increase the bioavailability of the drug and thereby improve the drug's ability. Compared with the prior art, crystalline form B and crystalline form C of the present disclosure have higher solubility and is favorable for drug development. Crystalline form B and crystalline form C of the present disclosure also have lower hygroscopicity than the prior art. Hydroscopic drug crystal form has weight changes due to adsorption of more water, so that determination of the content of crystalline component of the drug substance is not easy. In addition, the crystalline form of the drug substance absorbs water and lumps will form due to high hygroscopicity, which affects the particle size distribution thereof in the formulation process and the uniformity of the drug substance in the drug, thereby affecting the dissolution and bioavailability of the drug. Crystalline form B and crystalline form C of the present disclosure have substantially unchanged moisture content under different humidity conditions, and overcome the disadvantages caused by high hygroscopicity, which is more conducive to long-term storage of the drug, and reduces the costs of material storage and quality control.

Further, crystalline form B and crystalline form C of ODM-201 represented by formula (I) provided by the present disclosure have good stability, excellent flowability, optimal particle size with uniform distribution. The solvent used in the preparation of crystalline form B and crystalline form C of the present disclosure has lower toxicity, which is conducive to the green industrial production. Pharmaceutical risk brought by the toxic solvent residue is avoided and this is more conducive to the preparation of the drug product. The processes of the novel crystalline forms provided in the present disclosure are simple with short preparation period and without heating. This is favorable for cost control in production. Crystalline form B and crystalline form C of the present disclosure provide a new and better choice for the preparation of pharmaceutical formulations containing ODM-201, and are of great significance for drug development.

SUMMARY

Problems to be Solved by the Present Disclosure

The main objective of the present disclosure is to provide novel crystalline forms of ODM-201, processes for preparation and use thereof.

Solutions Provided by the Present Disclosure to Solve the Above Problems

According to the objective of the present disclosure, crystalline form B of ODM-201 represented by formula (I) is provided (hereinafter referred to as Form B).

The X-ray powder diffraction pattern of Form B shows characteristic peaks at 2theta values of 16.2°±0.2°, 9.0°±0.2° and 22.5°±0.2° using CuKα radiation.

Furthermore, the X-ray powder diffraction pattern of Form B shows 1 or 2 or 3 characteristic peaks at 2theta values of 24.7°±0.2°, 11.9°±0.2° and 18.1°±0.2°. Preferably, the X-ray powder diffraction pattern of Form B shows 3 characteristic peaks at 2theta values of 24.7°±0.2°, 11.9°±0.2° and 18.1°±0.2°.

Furthermore, the X-ray powder diffraction pattern of Form B shows 1 or 2 or 3 characteristic peaks at 2theta values of 14.7°±0.2°, 23.5°±0.2° and 27.8°±0.2°. Preferably, the X-ray powder diffraction pattern of Form B shows 3 characteristic peaks at 2theta values of 14.7°±0.2°, 23.5°±0.2° and 27.8°±0.2°.

In a preferred embodiment, the X-ray powder diffraction of Form B shows characteristic peaks at 2theta values of 16.2°±0.2°, 9.0°±0.2°, 22.5°±0.2°, 24.7°±0.2°, 11.9°±0.2°, 18.1°±0.2°, 14.7°±0.2°, 23.5°±0.2° and 27.8°±0.2°.

Without any limitation being implied, the X-ray powder diffraction pattern of Form B is substantially as depicted in FIG. 1.

According to the objective of the present disclosure, a process for preparing Form B is also provided. The process comprises: 1) Dissolving ODM-201 in an alcohol or ketone or a mixed solvent of alcohol and ketone, then adding water dropwise as anti-solvent until solid precipitated; or 2) Dissolving ODM-201 into mixed solvents of a halogenated hydrocarbon and an alcohol, or mixed solvents of an ether and water at room temperature, evaporating the clear solution at room temperature until solid precipitated.

Wherein:

Said alcohol is methanol, ethanol or mixture of methanol and ethanol,

Preferably, said alcohol is methanol;

Said halogenated hydrocarbon is chlorinated alkane;

Preferably, said chlorinated hydrocarbon is dichloromethane;

Said ketone solvent is saturated aliphatic ketone;

Preferably, said ketone is acetone;

Said ether is cyclic ether;

Preferably, said ether is tetrahydrofuran;

Preferably, the reaction temperature or operating temperature is 10-40° C., more preferably room temperature;

Preferably, the crystallization time is 36-72 hours, more preferably 48 hours.

According to the objective of the present disclosure, crystalline form C of ODM-201 represented by formula (I) is provided (hereinafter referred to as Form C).

The X-ray powder diffraction pattern of Form C shows characteristic peaks at 2theta values of 9.4°±0.2°, 14.1°±0.2° and 12.1°±0.2° using CuKα radiation.

Furthermore, the X-ray powder diffraction pattern of Form C shows 1 or 2 or 3 characteristic peaks at 2theta values of 15.1°±0.2°, 15.8°±0.2° and 19.9°±0.2°. Preferably, the X-ray powder diffraction pattern of Form C shows 3 characteristic peaks at 2theta values of 15.1°±0.2°, 15.8°±0.2° and 19.9°±0.2°.

Furthermore, the X-ray powder diffraction pattern of Form C shows characteristic peak at 2theta value of 23.7°±0.2°.

In a preferred embodiment, the X-ray powder diffraction of Form C shows characteristic peaks at 2theta values of 9.4°±0.2°, 14.1°±0.2°, 12.1°±0.2°, 15.1°±0.2°, 15.8°±0.2°, 19.9°±0.2° and 23.7°±0.2°.

Without any limitation being implied, the X-ray powder diffraction pattern of Form C is substantially as depicted in FIG. 8.

According to the objective of the present disclosure, a process for preparing Form C is also provided. The process comprises, but is not limited to: adding ODM-201 into a mixing system of acetic acid and other organic solvents at a certain volume ratio, and heating to a certain temperature, followed by cooling and crystallization.

Wherein:

Said other organic solvents include isopropanol, methyl tert-butyl ether, toluene and ethyl acetate.

Preferably, said other organic solvent is isopropanol or methyl tert-butyl ether;

Said heating temperature includes 40-60° C., preferably, the heating temperature is 50° C.;

Said volume ratio includes 2:1-1:2;

In the preparation method of Form B and Form C of the present disclosure:

Said ODM-201 free base or ODM-201 refers to the solid, semi-solid, wax or oil form of the compound of formula (I).

Said "room temperature" is not a specific temperature value and refers to a temperature range of 10-30° C.

Said "evaporating" is accomplished by using a conventional method in the field. For example, slow evaporation is to seal the container with a sealing film and puncture holes for evaporation; rapid evaporation is to place the container open for evaporation.

In the present disclosure, "crystal" or "crystalline form" refers to the crystal or the crystal form being identified by the X-ray diffraction pattern shown herein. Those skilled in the art are able to understand that physicochemical properties discussed herein can be characterized, wherein the experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and not intended to be used for absolute comparison. In addition, the experimental error of the diffraction peak angle is usually 5% or less, and the error of these angles should also be taken into account, and an error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. As used herein, "the same XRPD pattern" does not mean absolutely the same, the same peak positions may differ by ±0.2° and the peak intensity allows for some variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

"Crystalline form" and "polymorph" and other related terms are used in the present disclosure to mean that a solid compound exists in a specific crystalline state in a crystal structure. The difference in physical and chemical properties of polymorphs can be reflected in storage stability, compressibility, density, dissolution rate and the like. In extreme cases, differences in solubility or dissolution rate can cause drug inefficiencies and even toxicity.

In some embodiments, Form B or Form C of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and further more specifically less than 1% (w/w).

It should be noted that the numerical values and numerical ranges recited in the present disclosure are not to be construed as narrowly construed as a numerical value or a numerical range per se. It will be understood by those skilled in the art that they may vary depending on the specific technical environment without departing from the spirit of the disclosure. On the basis of the principle, there are fluctuations around specific numerical values. In the present disclosure, such a floating range which can be foreseen by those skilled in the art is often expressed by the term "about".

Advantageous Effect

Form B and Form C of the present disclosure have the following advantages compared with prior arts:

Form B and Form C of the present disclosure have weight gain of 1.07% and 0.93% at 80% relative humidity (RH), respectively. Form B and Form C are slightly hygroscopic. Compared with the prior arts, the crystalline forms of the present disclosure have lower hygroscopicity. Due to the low hygroscopicity, instability during drug preparation and/or storage and the un-processability of formulation caused by external factors such as environmental moisture can be avoided. Low hygroscopicity is advantageous for accurate quantification and later transportation and storage of the drug.

As can be seen from the stability test, Form B of the present disclosure is physically stable under the conditions of 25° C./60% RH and 40° C./75% RH for 3 months. Therefore, Form B of the present disclosure has good stability, which is advantageous for the storage and formulation process of the drug.

Compared with the crystalline form I disclosed in the prior art WO2016120530A1, Form B and Form C of the present disclosure can significantly improve the solubility, thereby contributing to an increase in the bioavailability of the drug.

Form B of the present disclosure has a narrower particle size distribution and a smaller particle size than crystalline form I. Its uniform particle size helps to simplify the post-treatment of the formulation process, such as decreasing the grinding of the crystal, saving cost, reducing the risk of crystallinity change and crystal transformation in the grinding, and improving the quality control. The narrower particle size distribution improves the uniformity of the drug substance components in the formulation, and reduces the variability in different batches to get more uniform dissolution. Its smaller crystalline particle size can increase the specific surface area of the drug substance, and improve the dissolution rate of the drug, thereby facilitating drug absorption and further improving the bioavailability of the drug.

Form C of the present disclosure has better grinding stability than the crystal form I of the prior art. Grinding and pulverization of the drug substance are often required in the formulation process. Better mechanical stability can reduce the risk of change in crystallinity of the drug substance during the formulation process.

Furthermore, the present disclosure provides a pharmaceutical composition comprising a therapeutically and/or prophylactically effective amount of Form B, Form C or combinations thereof, and at least one pharmaceutically acceptable carrier, diluent or excipient.

Further, the present disclosure provides the use of Form B and Form C of ODM-201 or combinations thereof for preparing drugs of androgen receptor antagonist.

Further, the present disclosure provides the use of Form B and Form C of ODM-201 or combinations thereof for preparing drugs for treating cancer.

Furthermore, the present disclosure provides the use of Form B and Form C of ODM-201 or combinations thereof for preparing drugs for treating prostate cancer.

The novel crystalline forms Form B or Form C of ODM-201 provided by the present disclosure have the following advantages: low hygroscopicity, good stability, excellent flowability, good grinding stability, optimal particle size with uniform distribution, and higher solubility compared with the prior art.

DETAILED DESCRIPTION OF THE DISCLOSURE

Figure 1:
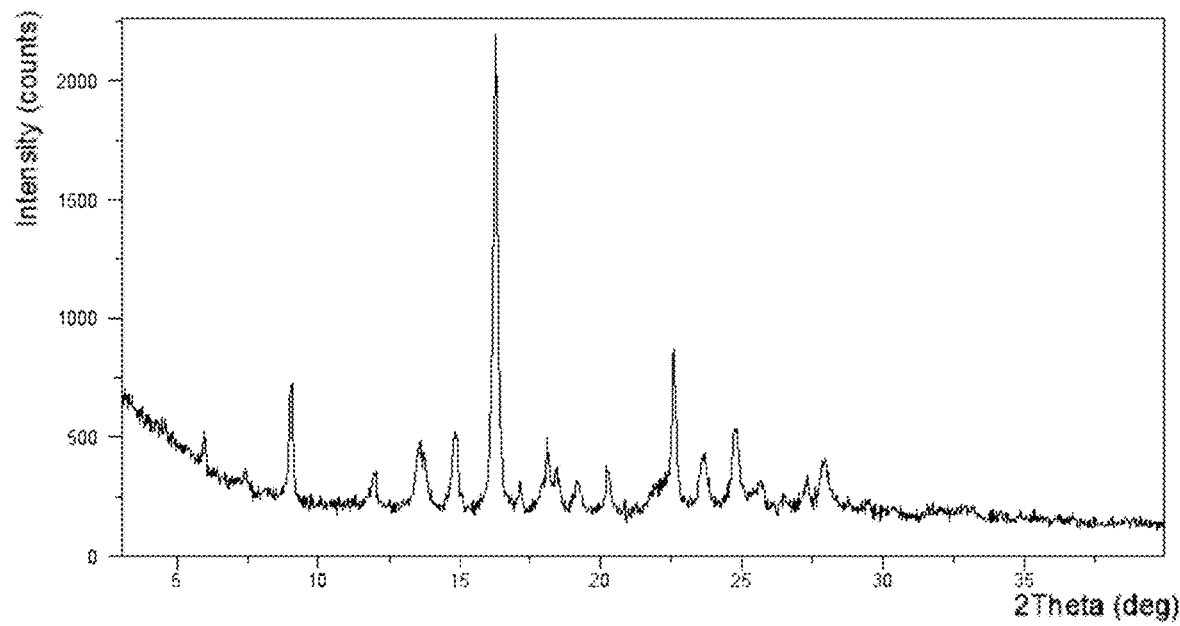
FIG. 1 shows an XRPD pattern of Form B according to example 1.

The present disclosure is further illustrated by the following examples which describe the preparation and uses of the crystalline forms of the disclosure in detail. It is obvious to those skilled in the art that many changes in the materials and methods can be accomplished without departing from the scope of the disclosure.

Instruments and methods used to collect data:

X-ray powder diffraction pattern in the present disclosure was acquired by a Panalytical Empyrean X-ray powder diffractometer. The parameters of the X-ray powder diffraction method of the present disclosure were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the differential scanning calorimetry (DSC) method of the present disclosure were as follows:

Heating rate: 10° C./min
Purge gas: nitrogen

Thermal gravimetric analysis (TGA) data in the present disclosure are acquired by a TA Q500. The parameters of the thermal gravimetric analysis (TGA) method of the present disclosure were as follow:

Heating rate: 10° C./min
Purge gas: nitrogen

Proton nuclear magnetic resonance spectrum data ($^1$H NMR) are collected from a Bruker Avance II DMX 400M HZ NMR spectrometer. 1-5 mg of sample was weighed, and dissolved in 0.5 mL of deuterated dimethyl sulfoxide or deuterated water to obtain a solution with a concentration of 2-10 mg/mL.

High Performance Liquid Chromatography (HPLC) data in the present disclosure are collected from Agilent 1260 with diode array detector (DAD).

The HPLC method parameters for solubility in the present disclosure are as follows:
1. Column: Agilent Infinity Lab Poroshell 120 EC-$C_{18}$ 150*3.0 mm, 2.7 μm
2. Mobile Phase: A: 25 mmol/L $KH_2PO_4$ aqueous solution
   B: Acetonitrile

| Gradient: | |
|---|---|
| Time (min) | % B |
| 0.0 | 30 |
| 6.0 | 45 |
| 7.0 | 80 |
| 10.0 | 80 |
| 10.1 | 30 |
| 12.0 | 30 |

3. Flow rate: 0.7 mL/min
4. Injection Volume: 5 μL
5. Detection wavelength: 220 nm
6. Column Temperature: 40° C.
7. Diluent: Acetonitrile/H$_2$O (v/v, 1/1)

The particle size distribution test in the present disclosure is acquired by the S3500 laser particle size analyzer of Microtrac. Microtrac S3500 is equipped with the SDC (Sample Delivery Controller). The test is carried out by wet process, and the dispersion medium is Isopar G. The parameters are as follows:

| | |
|---|---|
| Size distribution: Volume | Run Time: 10 s |
| Dispersion medium: Isopar G | Particle coordinates: Standard |
| Run Number: 3 times | Fluid refractive index: 1.42 |
| Particle Transparency: Trans | Residuals: Enabled |
| Particle refractive index: 1.5 | Flow rate: 60%* |
| Particle shape: Irregular | Filtration: Enabled |
| Ultrasonication power: 30 W | Ultrasonication time: 30 s |

*Flow rate 60% is 60% of 65 mL/s.

Unless otherwise specified, the following examples were conducted at room temperature.

The starting material ODM-201 used in the following examples can be prepared according to the method described in the prior art, for example, the method disclosed in CN102596910B.

Form I used in the following examples was prepared according to the method disclosed in WO2016120530A1.

EXAMPLE 1: PREPARATION OF FORM B 29.5 mg of ODM-201 solid was added into 1.0 mL of dichloromethane/methanol (1:1, v/v) at room temperature to obtain a clear solution, and the solution was evaporated at room temperature for about 5 days until solid precipitated.

The obtained solid in this example was confirmed to be Form B. The XRPD data are listed in
Table 1, and the XRPD pattern is substantially as depicted in FIG. 1.

TABLE 1

| 2 theta | d spacing | Intensity % |
|---|---|---|
| 5.89 | 15.00 | 5.85 |
| 7.32 | 12.08 | 2.49 |
| 8.96 | 9.87 | 23.95 |
| 11.89 | 7.45 | 6.75 |
| 13.46 | 6.58 | 12.79 |
| 14.78 | 5.99 | 15.21 |
| 16.20 | 5.47 | 100.00 |
| 17.06 | 5.20 | 4.98 |
| 18.03 | 4.92 | 14.32 |
| 18.38 | 4.83 | 7.76 |
| 19.11 | 4.65 | 6.18 |
| 20.17 | 4.40 | 8.33 |
| 22.51 | 3.95 | 31.86 |
| 23.54 | 3.78 | 11.12 |
| 24.67 | 3.61 | 16.83 |
| 25.62 | 3.48 | 6.10 |
| 27.23 | 3.28 | 6.08 |
| 27.87 | 3.20 | 10.27 |

EXAMPLE 2: PREPARATION OF FORM B 31.6 mg of ODM-201 solid was added into 1.2 mL of dichloromethane/methanol (1:2, v/v) at room temperature to obtain a clear solution, and the solution was evaporated at room temperature for about 5 days until solid precipitated.

Figure 2:
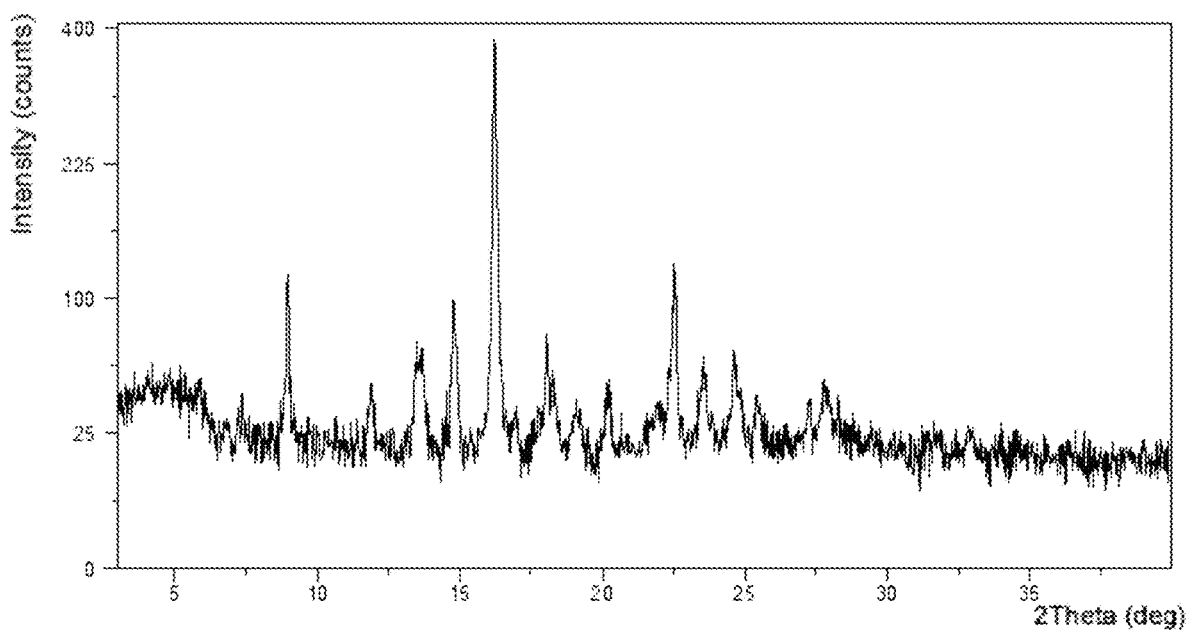
FIG. 2 shows an XRPD pattern of Form B according to example 2.

The solid obtained in this example was confirmed to be Form B. The XRPD data are listed in Table 2, and the XRPD pattern is substantially as depicted in FIG. 2.

TABLE 2

| 2 theta | d spacing | Intensity % |
|---|---|---|
| 8.96 | 9.87 | 24.75 |
| 11.86 | 7.46 | 5.76 |
| 13.56 | 6.53 | 10.98 |
| 14.78 | 5.99 | 18.86 |
| 16.23 | 5.46 | 100.00 |
| 18.13 | 4.89 | 9.71 |
| 20.19 | 4.40 | 6.01 |
| 22.52 | 3.95 | 28.70 |
| 23.57 | 3.77 | 8.23 |
| 24.66 | 3.61 | 9.07 |
| 27.82 | 3.21 | 5.69 |

Figure 3:
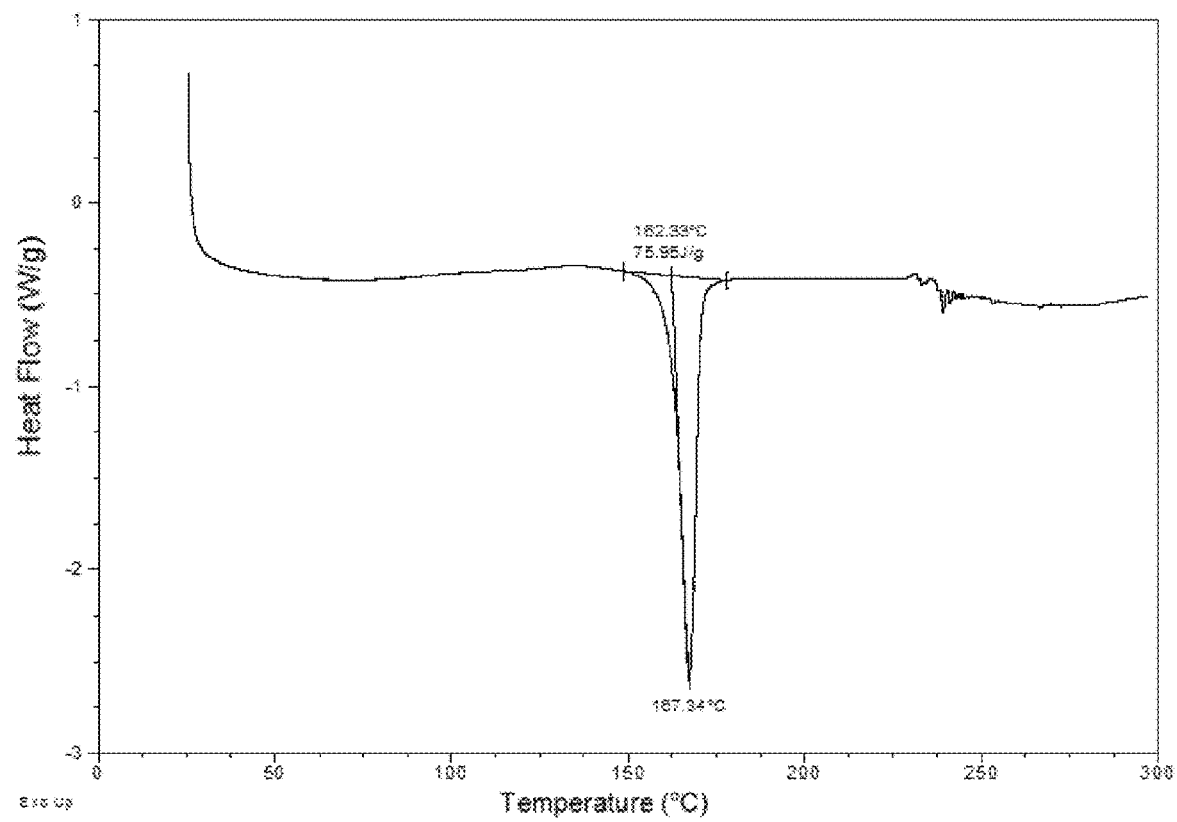
FIG. 3 shows a DSC curve of Form B according to example 2.

The DSC curve of Form B is substantially as depicted in FIG. 3, which comprises one endothermic peak at around 162° C. corresponding to the melting process.

Figure 4:
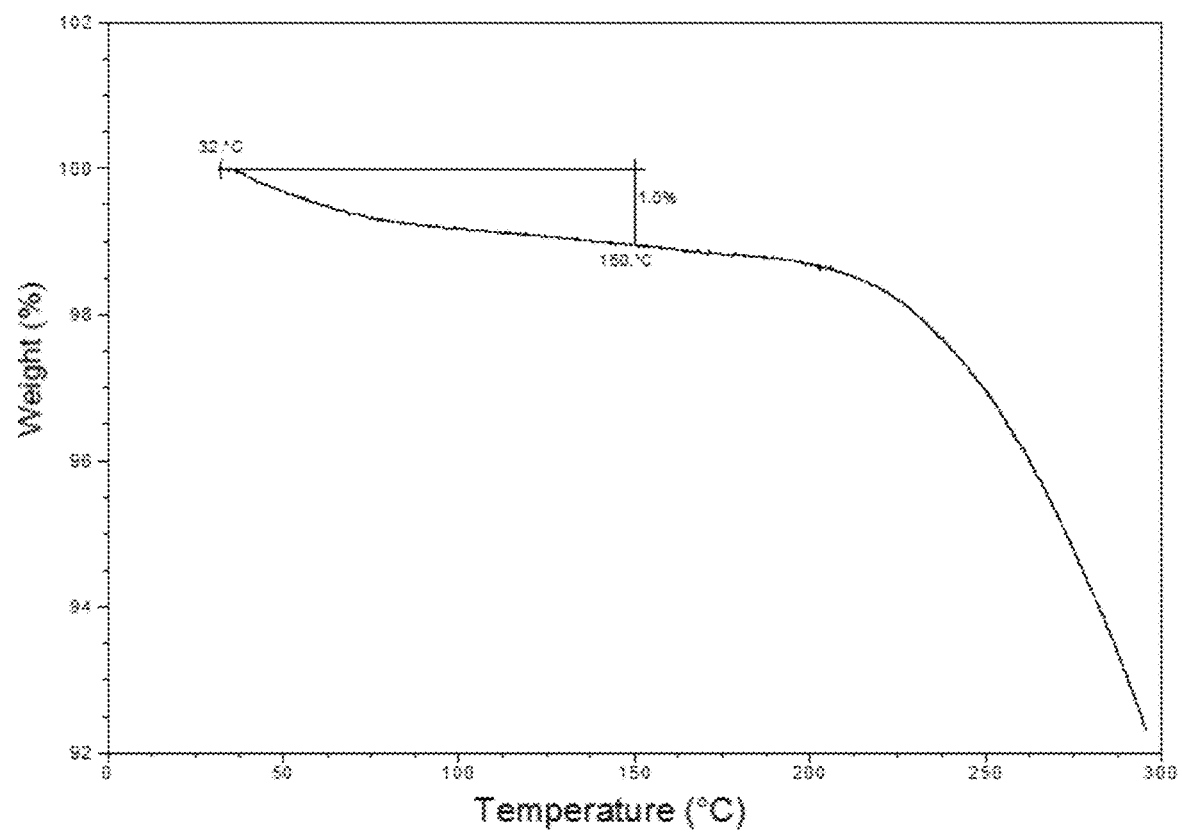
FIG. 4 shows a TGA curve of Form B according to example 2.

The TGA curve of Form B is substantially as depicted in FIG. 4, which shows about 1.0% weight loss when heated to 150° C.

EXAMPLE 3: PREPARATION OF FORM B 20.3 mg of ODM-201 solid was dissolved in 0.8 mL of acetone, and then 4.0 mL of water was added dropwise with solid precipitated.

Figure 5:
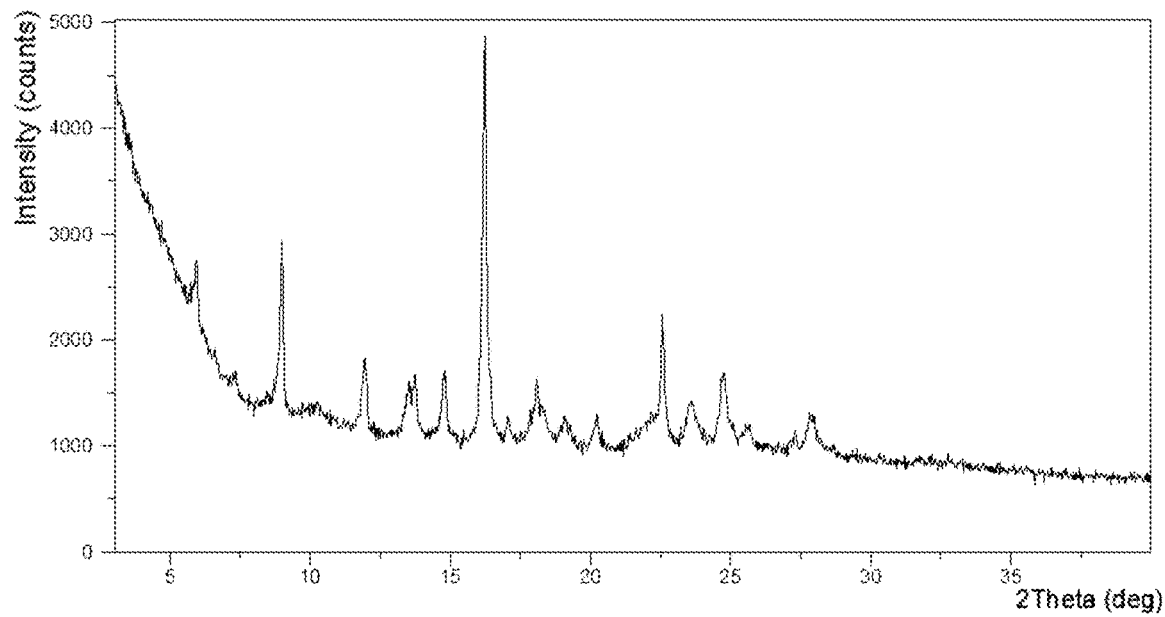
FIG. 5 shows an XRPD pattern of Form B according to example 3.
Figure 6:
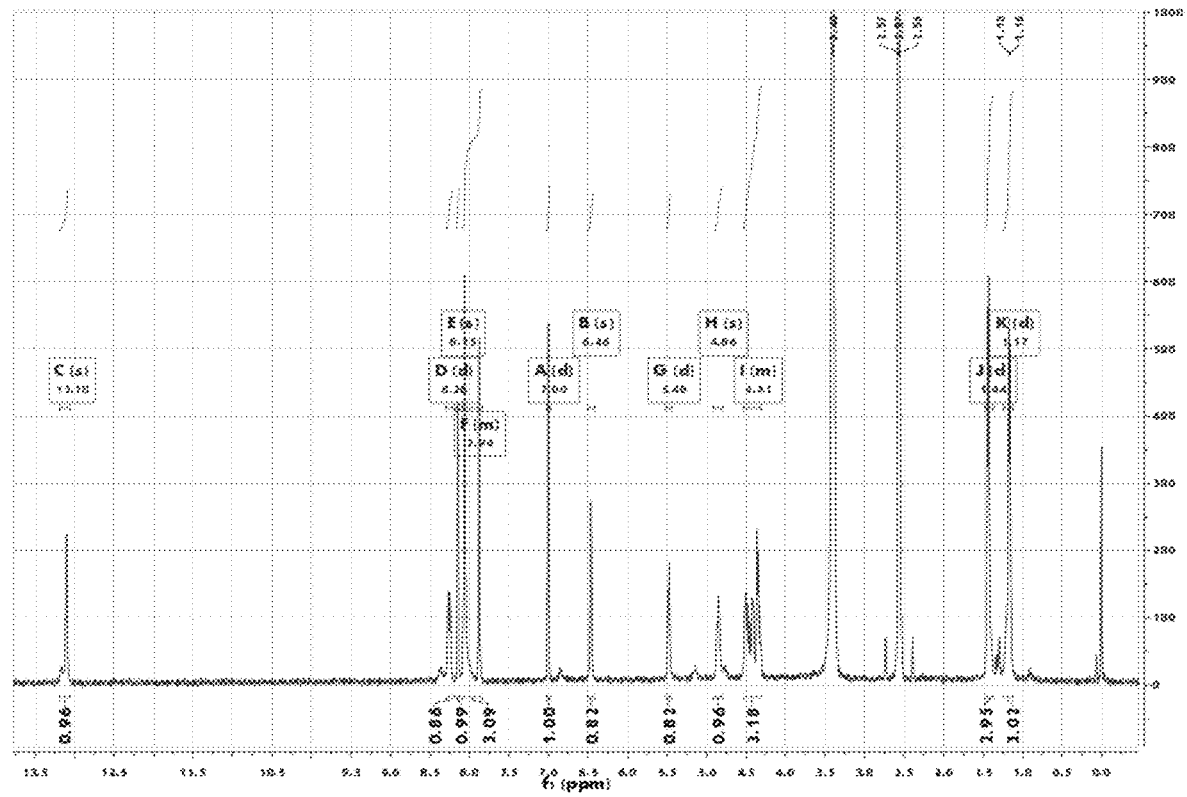
FIG. 6 shows a $^1$H NMR spectrum of Form B according to example 3.

The solid obtained in this example was confirmed to be Form B. The XRPD data are listed in Table 3, and the XRPD pattern is substantially as depicted in FIG. 5. The chemical structure was determined by liquid NMR, and the corresponding data are: $^1$H NMR (400 MHz, DMSO) δ 13.10 (s, 1H), 8.26 (d, J=8.6 Hz, 1H), 8.15 (s, 1H), 8.08-7.85 (m, 3H), 7.00 (d, J=2.1 Hz, 1H), 6.46 (s, 1H), 5.48 (d, J=4.6 Hz, 1H), 4.86 (s, 1H), 4.55-4.31 (m, 3H), 1.44 (d, J=6.4 Hz, 3H), 1.17 (d, J=6.3 Hz, 3H). The $^1$H NMR spectrum is substantially as depicted in FIG. 6.

TABLE 3

| 2 theta | d spacing | Intensity % |
|---|---|---|
| 5.88 | 15.02 | 12.07 |
| 8.96 | 9.87 | 39.59 |
| 10.11 | 8.75 | 2.63 |
| 11.91 | 7.43 | 16.39 |
| 13.70 | 6.46 | 15.35 |
| 14.74 | 6.01 | 15.50 |
| 16.20 | 5.47 | 100.00 |
| 17.02 | 5.21 | 5.92 |
| 18.05 | 4.91 | 15.51 |
| 19.03 | 4.66 | 6.54 |
| 20.16 | 4.40 | 7.43 |
| 22.52 | 3.95 | 31.50 |
| 23.52 | 3.78 | 11.99 |
| 24.72 | 3.60 | 19.12 |
| 25.55 | 3.49 | 6.12 |
| 27.83 | 3.21 | 8.69 |

EXAMPLE 4: PREPARATION OF FORM B 26.5 mg of ODM-201 solid was added into 1.8 mL of tetrahydrofuran/water (4:1, v/v) at room temperature to obtain a clear solution, and the solution was evaporated at room temperature for about 5 days until solid precipitated.

Figure 7:
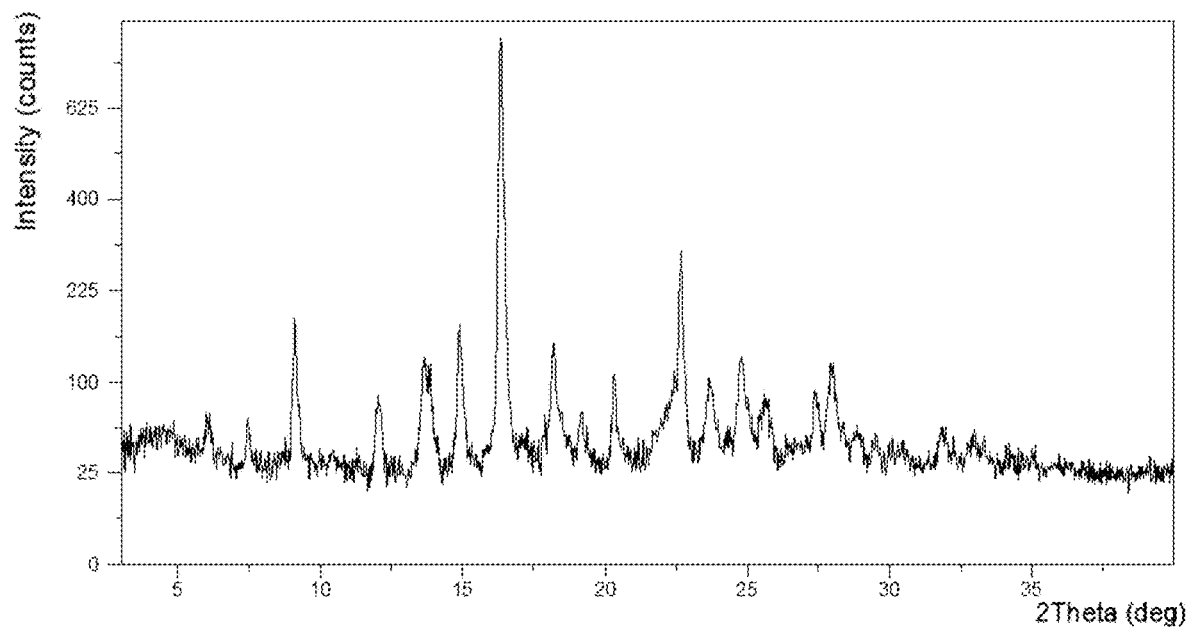
FIG. 7 shows an XRPD pattern of Form B according to example 4.

The solid obtained in this example was confirmed to be Form B. The XRPD data are listed in Table 4, and the XRPD pattern is substantially as depicted in FIG. 7.

TABLE 4

| 2 theta | d spacing | Intensity % |
|---|---|---|
| 5.94 | 14.88 | 3.21 |
| 7.33 | 12.06 | 3.60 |
| 8.96 | 9.87 | 19.24 |
| 11.88 | 7.45 | 6.40 |
| 13.49 | 6.56 | 12.22 |
| 14.75 | 6.01 | 17.06 |
| 16.21 | 5.47 | 100.00 |
| 18.09 | 4.90 | 14.73 |
| 19.06 | 4.66 | 5.04 |
| 20.17 | 4.40 | 10.14 |
| 22.53 | 3.95 | 32.74 |
| 23.59 | 3.77 | 7.95 |
| 24.65 | 3.61 | 12.34 |
| 25.53 | 3.49 | 6.32 |
| 27.25 | 3.27 | 7.42 |
| 27.85 | 3.20 | 10.63 |
| 28.76 | 3.10 | 3.15 |
| 31.73 | 2.82 | 2.82 |
| 32.93 | 2.72 | 1.48 |

EXAMPLE 5: PREPARATION OF FORM C 33.7 mg of ODM-201 solid was added into 2.0 mL of acetic acid/isopropanol (1:2, v/v). The above mixture was kept at 50° C. for 5 hours, then filtered and rapidly cooled to 4° C. to obtain a white solid.

Figure 8:
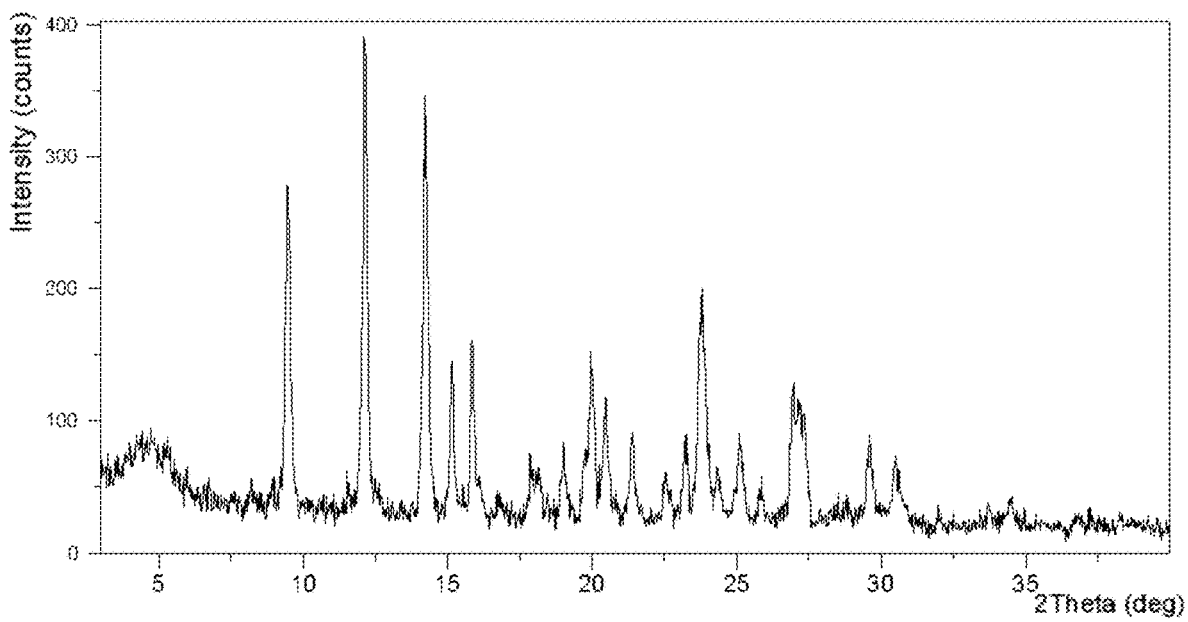
FIG. 8 shows an XRPD pattern of Form C according to example 5.

The solid obtained in this example was confirmed to be Form C. The XRPD data are listed in Table 5, and the XRPD pattern is substantially as depicted in FIG. 8.

TABLE 5

| 2 theta | d spacing | Intensity % |
|---|---|---|
| 4.50 | 19.62 | 7.28 |
| 9.40 | 9.41 | 69.13 |
| 12.06 | 7.34 | 100.00 |
| 14.14 | 6.26 | 74.33 |
| 15.07 | 5.88 | 33.33 |
| 15.78 | 5.61 | 37.25 |
| 17.95 | 4.94 | 7.11 |
| 18.91 | 4.69 | 10.70 |
| 19.93 | 4.46 | 31.90 |
| 20.39 | 4.36 | 24.61 |
| 21.32 | 4.17 | 18.11 |
| 22.51 | 3.95 | 7.52 |
| 23.20 | 3.83 | 18.32 |
| 23.68 | 3.76 | 44.42 |
| 25.04 | 3.56 | 17.65 |
| 25.78 | 3.46 | 7.02 |
| 26.86 | 3.32 | 26.38 |
| 27.26 | 3.27 | 21.55 |
| 29.50 | 3.03 | 15.43 |
| 30.44 | 2.94 | 12.15 |
| 34.43 | 2.60 | 4.21 |

EXAMPLE 6: PREPARATION OF FORM C 29.5 mg of ODM-201 solid was added into 2.0 mL of acetic acid/isopropanol (1:1, v/v). The above mixture was kept at 50° C. for 5 hours, then filtered and rapidly cooled to 4° C. to obtain a white solid.

Figure 9:
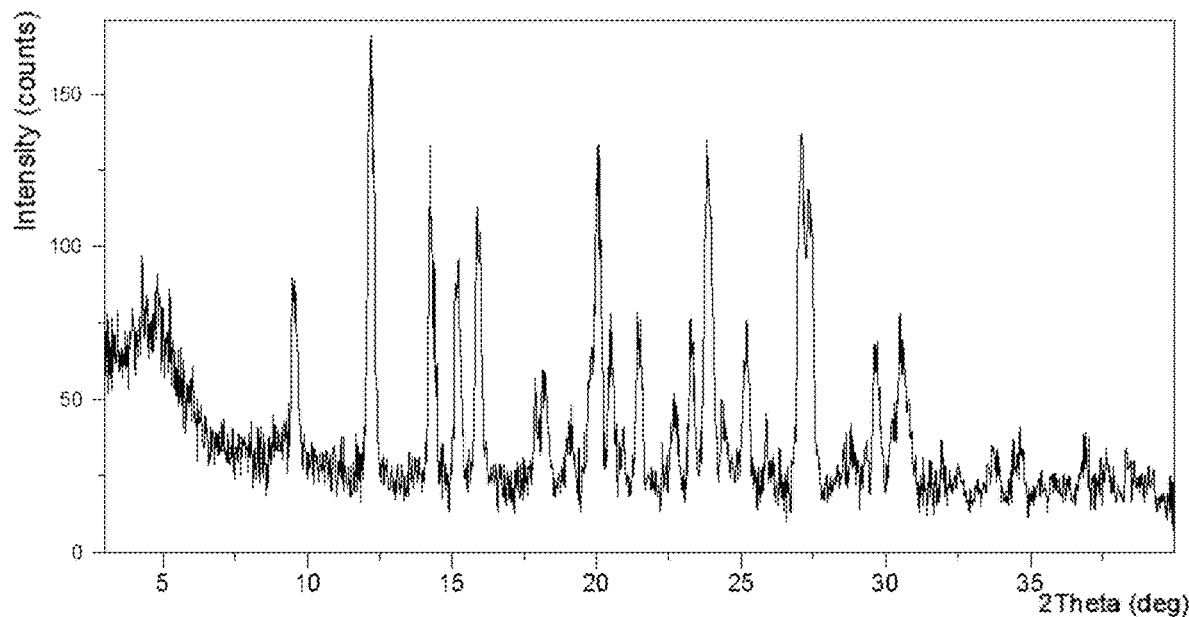
FIG. 9 shows an XRPD pattern of Form C according to example 6.

The solid obtained in this example was confirmed to be Form C. The XRPD data are listed in Table 6, and the XRPD pattern is substantially as depicted in FIG. 9.

TABLE 6

| 2 theta | d spacing | Intensity % |
|---|---|---|
| 9.42 | 9.39 | 41.55 |
| 12.07 | 7.34 | 100.00 |
| 14.14 | 6.26 | 75.78 |
| 15.07 | 5.88 | 47.86 |
| 15.82 | 5.60 | 56.51 |
| 18.16 | 4.88 | 22.96 |
| 19.01 | 4.67 | 12.60 |
| 19.97 | 4.45 | 72.50 |
| 20.40 | 4.35 | 35.66 |
| 21.35 | 4.16 | 38.06 |
| 22.53 | 3.95 | 15.90 |
| 23.18 | 3.84 | 36.51 |
| 23.68 | 3.76 | 73.07 |
| 25.10 | 3.55 | 36.13 |
| 26.95 | 3.31 | 73.82 |
| 27.32 | 3.26 | 63.99 |
| 29.54 | 3.02 | 31.32 |
| 30.47 | 2.93 | 35.53 |
| 33.60 | 2.67 | 8.62 |
| 34.57 | 2.59 | 11.73 |

EXAMPLE 7: PREPARATION OF FORM C 12.45 mg of ODM-201 free base was added into 0.2 mL of acetic acid/methyl tert-butyl ether (1:2, v/v). The above mixture was kept at 50° C. for 5 hours, then filtered and rapidly cooled to 4° C. to obtain a white solid. The solid obtained in this example was confirmed to be Form C.

EXAMPLE 8: HYGROSCOPICITY OF FORM B, FORM C AND CRYSTALLINE FORM I IN THE PRIOR ART

Figure 10:
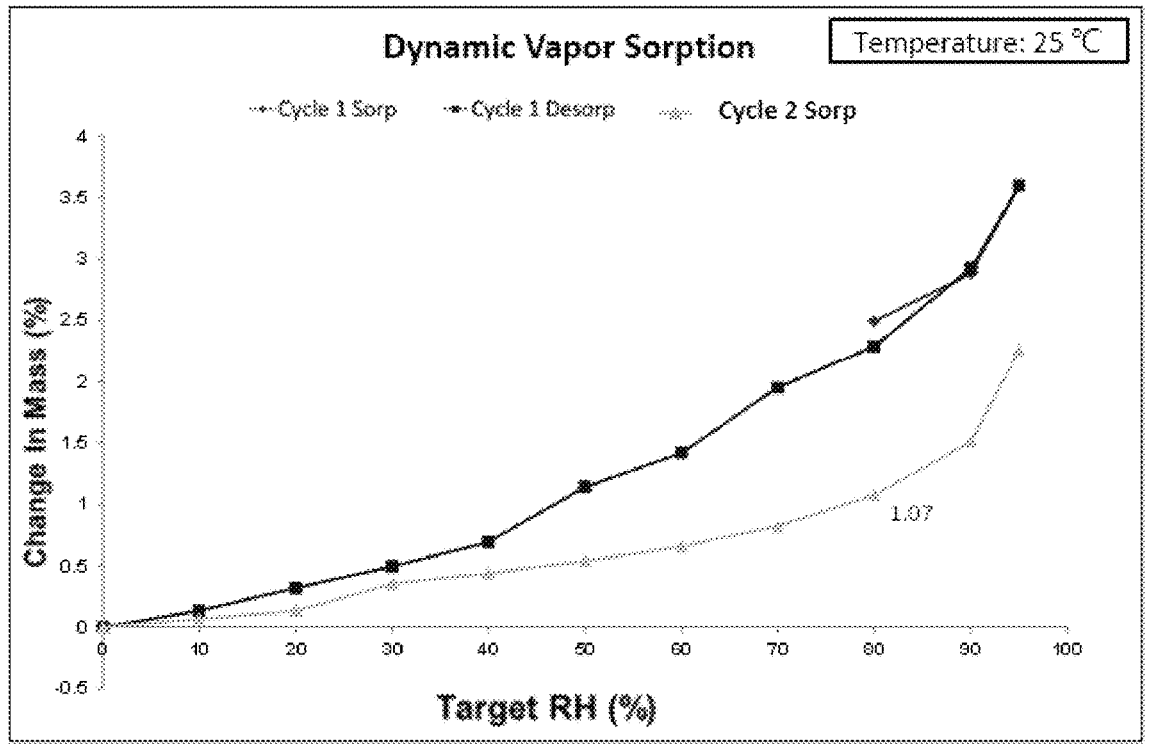
FIG. 10 shows a DVS plot of Form B.
Figure 11:
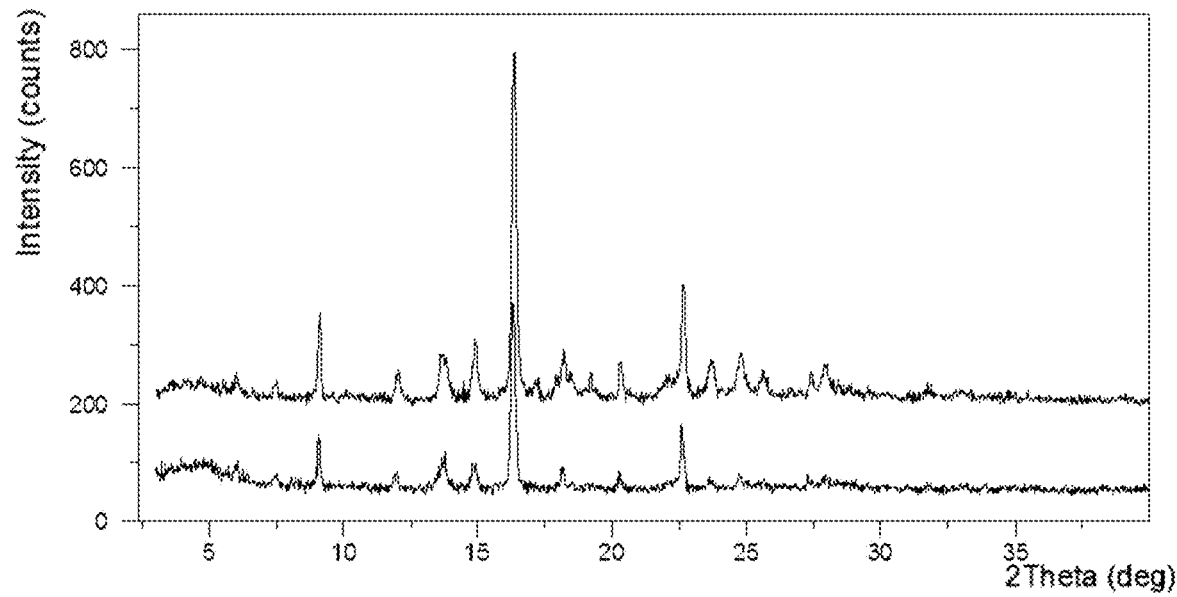
FIG. 11 shows an XRPD pattern overlay of Form B before and after DVS test (top: XRPD pattern after DVS, bottom: XRPD pattern before DVS).
Figure 12:
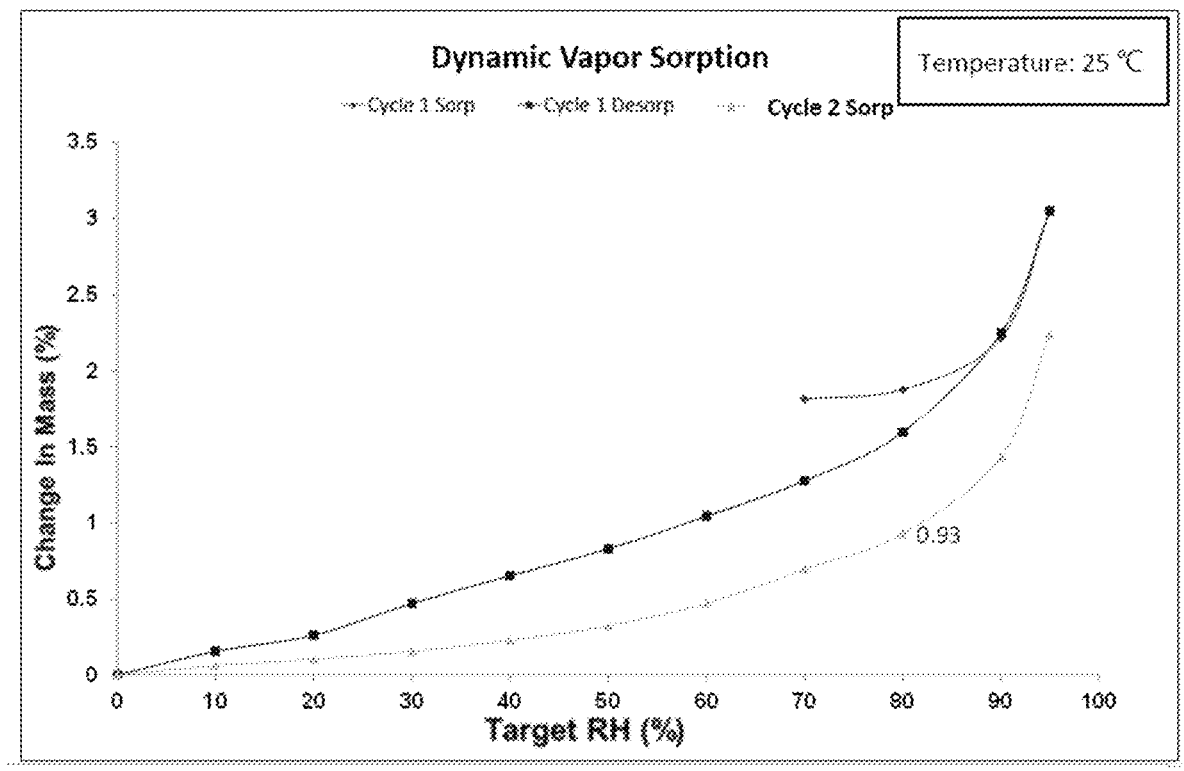
FIG. 12 shows a DVS plot of Form C.
Figure 13:
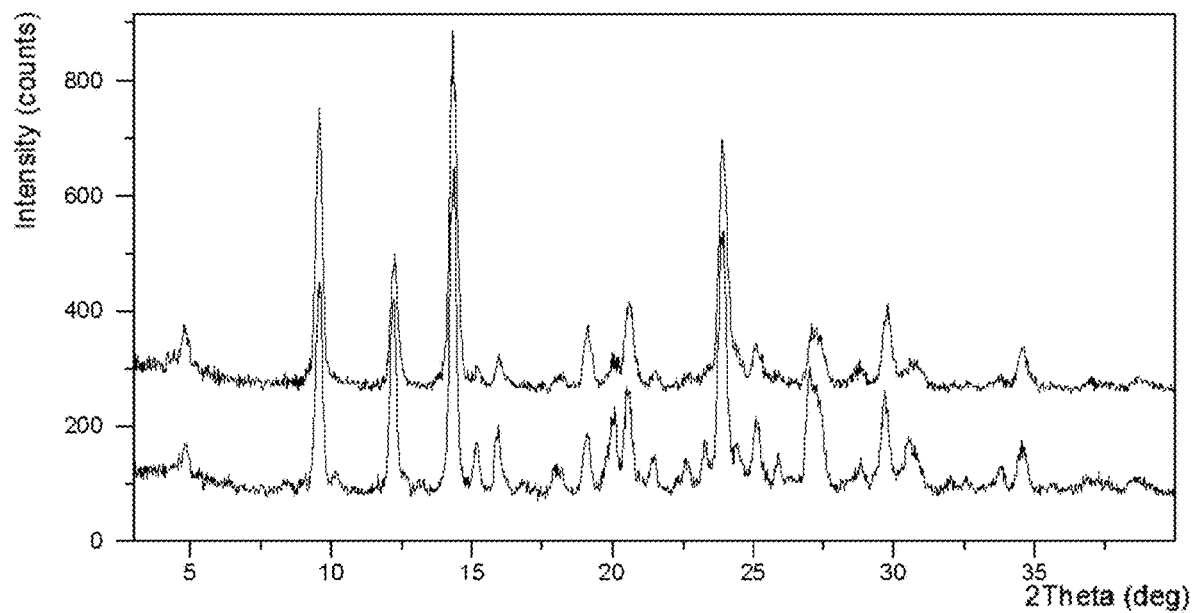
FIG. 13 shows an XRPD pattern overlay of Form C before and after DVS test (top: XRPD pattern after DVS, bottom: XRPD pattern before DVS).
Figure 14:
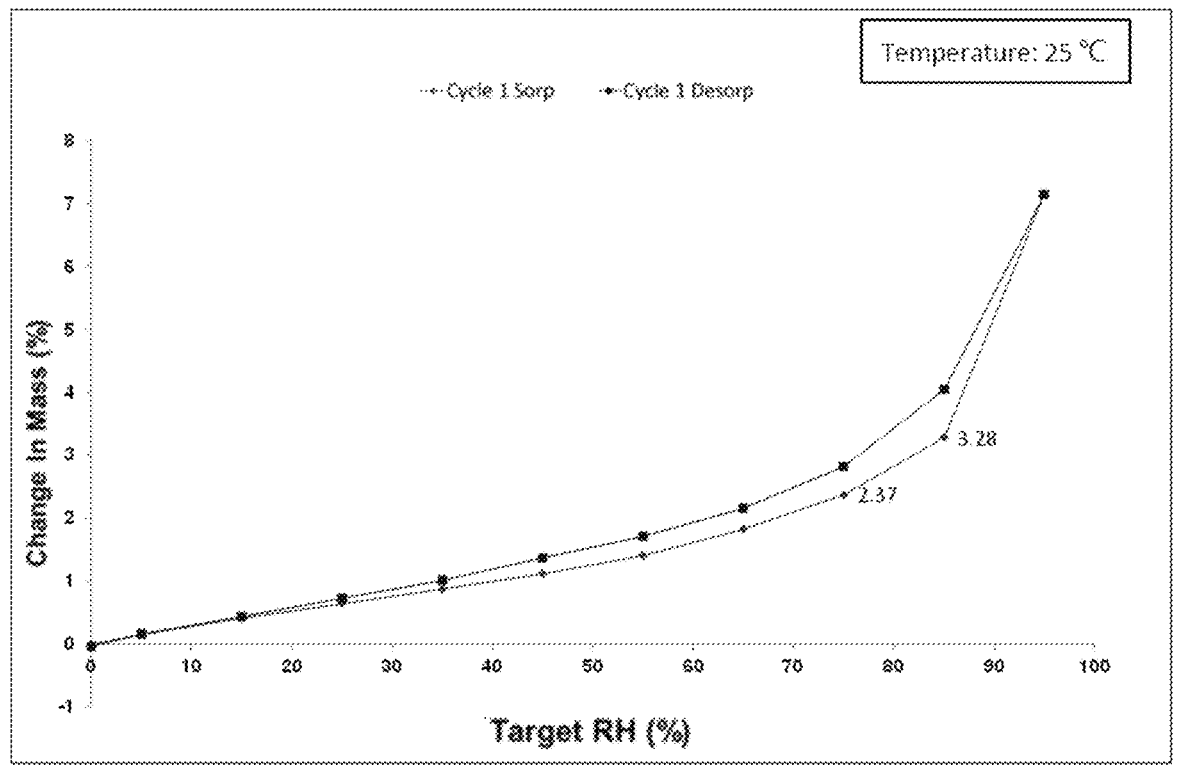
FIG. 14 shows a DVS plot of crystalline form I in the prior art.

Dynamic vapor sorption (DVS) was applied to test hygroscopicity of Form B, Form C and crystalline form I in the prior art with about 10 mg of samples. The results were listed in Table 7. The DVS plot of Form B is substantially as depicted in FIG. 10 and the XRPD pattern overlay before and after DVS test of Form B is substantially as depicted in FIG. 11. The DVS plot of Form C is substantially as depicted in FIG. 12 and the XRPD pattern overlay before and after DVS test of Form C is substantially as depicted in FIG. 13. The DVS plot of crystalline form I in the prior art is substantially as depicted in FIG. 14.

TABLE 7

| | Weight gain under 80% RH | Hygroscopicity | Solid Form after DVS |
|---|---|---|---|
| Form B | 0.93% | slightly hygroscopic | Form B (as shown in FIG. 11, top) |
| Form C | 1.60% | slightly hygroscopic | Form C (as shown in FIG. 13, top) |
| Crystalline form I | >2.37% | hygroscopic | — |

Hygroscopicity is one of the key properties for crystalline drug substance. Crystalline drug substance with high hygroscopicity tends to show weight change due to water absorption, thereby causing difficulty in determining the content of active pharmaceutical ingredients in the drug substance. In addition, the crystalline form of the drug substance absorbs water and lumps will form due to high hygroscopicity, which affects the particle size distribution thereof in the formulation process and the uniformity of active pharmaceutical ingredients in the drug products, thereby affecting the dissolution and bioavailability of the drug. The highly hygroscopic drug substance needs special packaging and storage conditions, thus increasing the cost of drug preparation. Therefore, crystalline form with low hygroscopicity is essential for drug preparation.

The result shows that Form B and Form C of the present disclosure have lower hygroscopicity compared with the prior art, and crystalline forms of Form B and Form C remain unchanged after DVS test, so that the above-mentioned disadvantages caused by high hygroscopicity can be overcome. The drug preparation and post-treatment processes can be simplified with no need for humidity control in the formulation process, special requirements for packaging and storage conditions, thus saving cost, benefiting industrial production and long-term storage. Without strict requirements for storage condition, the material storage and quality control costs can be greatly reduced, which have strong economic value and makes Form B and Form C more suitable for drug application.

Description and definition of hygroscopicity (Chinese Pharmacopoeia 2015 edition appendix Drug hygroscopic test guidelines, test at 25° C.+/−1° C., 80% RH).

Deliquescent: Sufficient water is absorbed to form a liquid;

Very hygroscopic: Increase in mass is equal to or greater than 15 percent;

Hygroscopic: Increase in mass is less than 15 percent and equal to or greater than 2 percent;

Slightly hygroscopic: Increase in mass is less than 2 percent and equal to or greater than 0.2 percent.

Non-hygroscopic or almost non-hygroscopic: Increase in mass is less than 0.2%.

EXAMPLE 9: STABILITY OF FORM B AND FORM C

Figure 15:
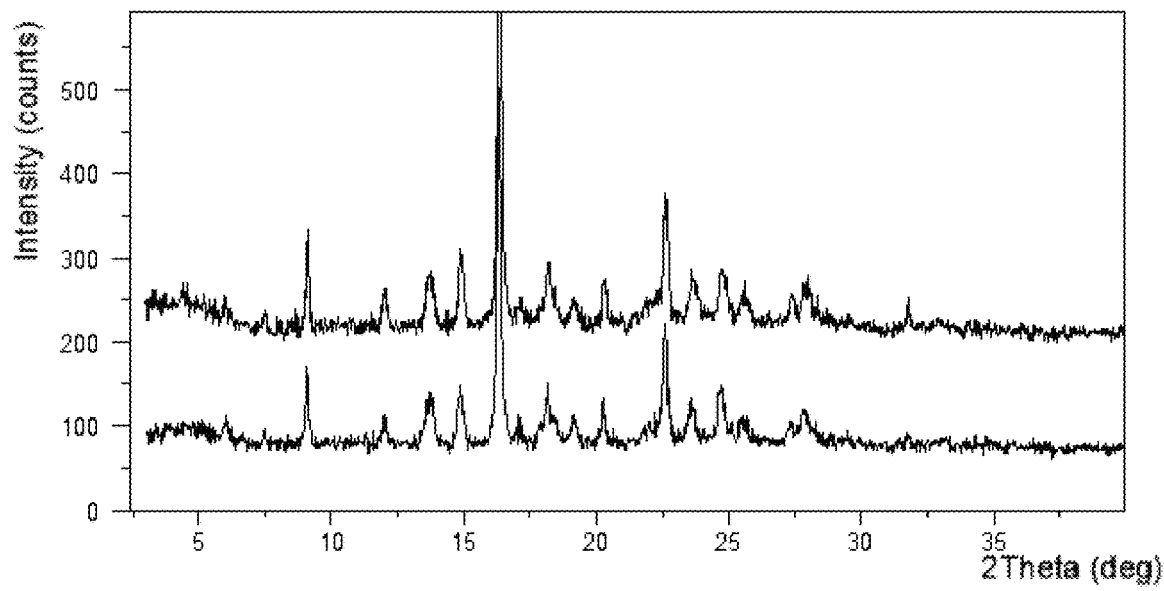
FIG. 15 shows an XRPD pattern overlay of Form B before and after stored at 25° C./60% RH (top: XRPD pattern after stored at 25° C./60% RH, bottom: XRPD pattern before stored at 25° C./60% RH).
Figure 16:
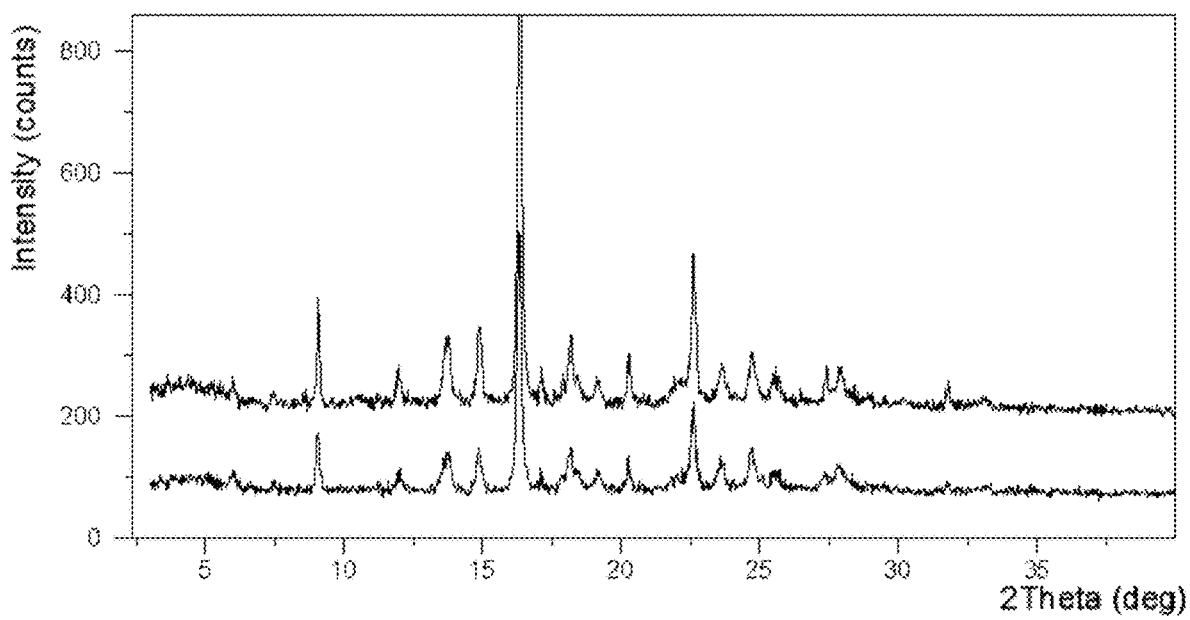
FIG. 16 shows an XRPD pattern overlay of Form B before and after stored at 40° C./75% RH (top: XRPD pattern after stored at 40° C./75% RH, bottom: XRPD pattern before stored at 40° C./75% RH).

Samples of Form B were stored under different conditions of 25° C./60% RH (open), 40° C./75% RH (open) for 3 months, and XRPD was applied to test the crystalline form. The XRPD patterns before and after stored for 3 months are shown in FIG. 15 and FIG. 16. The results were shown in Table 8.

TABLE 8

| Initial Solid Form | Storage Condition | Time | Change of Solid Form |
|---|---|---|---|
| Form B (FIG. 15, bottom) | 25° C./60% RH | 3 months | Form B remained unchanged (FIG. 15, top) |
| Form B (FIG. 16, bottom) | 40° C./75% RH | 3 months | Form B remained unchanged (FIG. 16, top) |

Form B keeps stable for at least 3 months at 25° C./60% RH and 40° C./75% RH. It can be seen that Form B has good stability.

Figure 17:
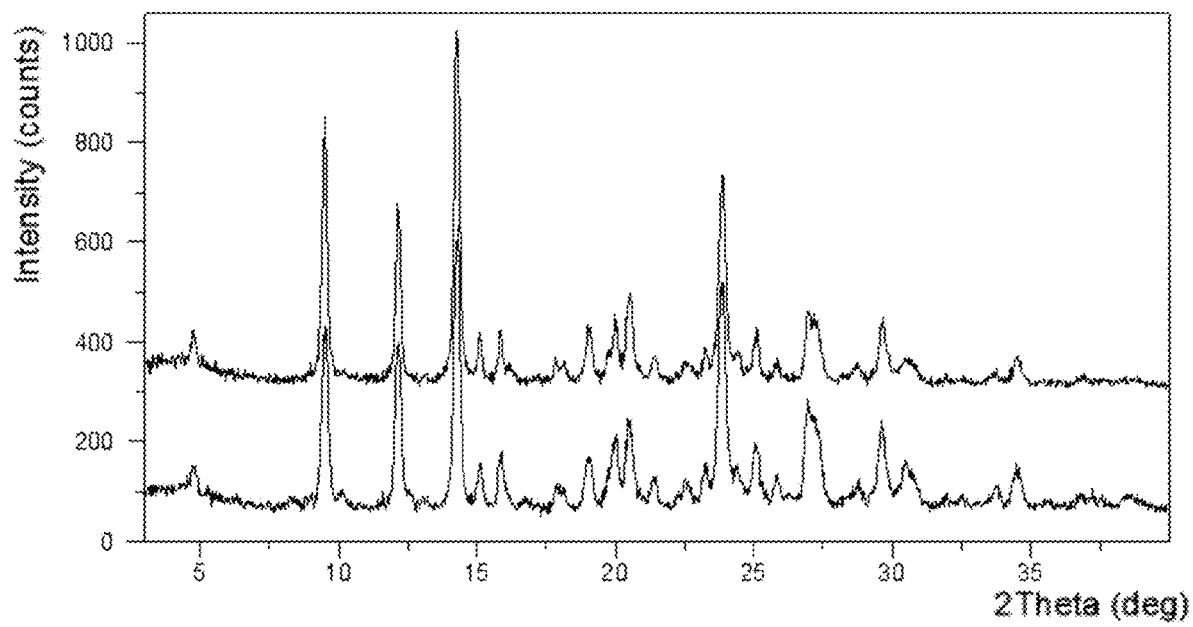
FIG. 17 shows an XRPD pattern overlay of Form C before and after stored at 25° C./60% RH (top: XRPD pattern after stored at 25° C./60% RH, bottom: XRPD pattern before stored at 25° C./60% RH).

Samples of Form C were stored at 25° C./60% RH (open) for 1 month, and XRPD was applied to test the crystalline form. The XRPD patterns before and after stored for 1 month were shown in FIG. 17. The results were shown in Table 9.

TABLE 9

| Initial Solid Form | Storage Condition | Time | Change of Solid Form |
|---|---|---|---|
| Form C (FIG. 17, bottom) | 25° C./60% RH | 1 month | Form C remained unchanged (FIG. 17, top) |

Form C keeps stable for at least 1 month at 25° C./60% RH. It can be seen that Form C has good stability.

The stability of drug is very important, especially during the shelf life of the drug in market. Good stability could reduce the risk of the crystal transformation which may cause the change of drug dissolution rate and bioavailability, and is of great significance to ensure the efficacy and safety of the drug and prevent the occurrence of adverse drug reactions. Crystalline form with better stability is controllable during the crystallization process and not easy to produce mixed crystal. Meanwhile, during the formulation and storage processes, crystalline form with better stability is hard to convert into other crystal forms. As a result, consistent and controllable of product quality can be ensured, and the dissolution profile will not change with the storage time.

The results show that Form B and Form C in the present disclosure have good stability and meet the stringent requirements in the drug application and formulation process.

EXAMPLE 10: SOLUBILITY COMPARISON OF FORM B IN THE PRESENT DISCLOSURE AND CRYSTALLINE FORM I IN THE PRIOR ART

Solubility is one of the key properties of drugs, which directly affects the absorption of drugs in the human body. The solubility of different crystalline forms may have obvious difference, and the absorption dynamics in vivo may also change, resulting in differences in bioavailability, which ultimately affects the clinical safety and efficacy of the drug.

Solubility increase for a poorly soluble drug is especially important. The increase of solubility of the drug will help to improve bioavailability, and make it easy for drug preparation. In addition, the increase of solubility also reduces the difficulty of formulation process. Crystalline form with sufficiently high solubility can be developed using conventional formulation process, while for a less soluble crystalline form, more complex formulation processes are needed in order to achieve ideal bioavailability. Moreover, the improvement in solubility can reduce the dose of the drug while ensuring its efficacy, thereby reducing the side effects and improving the safety of the drug.

The following experiment was conducted in order to test the solubility of Form B in the present disclosure:

Samples of Form B in the present disclosure and crystalline form I disclosed in WO2016120530A1 were suspended into SGF (simulated gastric fluids, pH=1.8), FeSSIF (Fed state simulated intestinal fluids, pH=5.0) and FaSSIF (Fasted state simulated intestinal fluids, pH=6.5) to get saturated solutions. After equilibrated for 1 hour and 4 hours, concentrations of the saturated solutions were measured by HPLC. The results were listed in Table 10.

TABLE 10

|  |  | SGF | | FeSSIF | | FaSSIF | |
|---|---|---|---|---|---|---|---|
|  | Time | Form B | crystalline form I | Form B | crystalline form I | Form B | crystalline form I |
| Solubility (μg/mL) | 1 hour | 62.7 | 14.0 | 408.1 | 183.1 | 3.0 | 1.0 |
|  | 4 hours | 33.5 | 9.9 | 288.0 | 206.3 | 0.5 | 0.1 |

The results show that the solubility of Form B of the present disclosure in SGF, FaSSIF and FeSSIF for 1 hour and 4 hours are significantly higher than that of Form I disclosed in WO2016120530A1.

Dissolution is needed before in vivo absorption of drugs. From the above results, the solubility of crystalline form I is low, so it is very important to improve the solubility of crystalline drugs. Compared with the prior art, the solubility of Form B in the present disclosure is remarkably improved, providing a better choice for drug development.

EXAMPLE 11: SOLUBILITY COMPARISON OF FORM C IN THE PRESENT DISCLOSURE AND CRYSTALLINE FORM I IN THE PRIOR ART

Samples of Form C in the present disclosure and crystalline form I disclosed in WO2016120530A1 were suspended into FeSSIF (Fed state simulated intestinal fluids, pH=5.0) and FaSSIF (Fasted state simulated intestinal fluids, pH=6.5) to get saturated solutions. After equilibrated for 1 hour and 4 hours, concentrations of the saturated solutions were measured by HPLC. The results are listed in Table 11.

TABLE 11

|  |  | FeSSIF | | FaSSIF | |
|---|---|---|---|---|---|
|  | Time | Form C | Crystalline form I | Form C | Crystalline form I |
| Solubility (μg/mL) | 1 hour | 469.6 | 183.1 | 39.0 | 1.0 |
|  | 4 hours | 163.1 | 206.3 | 35.5 | 0.1 |

The results show that the solubility of Form C of the present disclosure in FeSSIF (1 h) and FaSSIF (1 h and 4 h) are significantly higher than that of crystalline form I disclosed in WO2016120530A1. Compared with the prior art, Form C in the present disclosure has a higher solubility, providing a better choice for drug development.

EXAMPLE 12: PARTICLE SIZE DISTRIBUTION COMPARISON OF FORM B IN THE PRESENT DISCLOSURE AND CRYSTALLINE FORM I IN THE PRIOR ART

The particle size distribution of Form B in the present disclosure and Form I disclosed in WO2016120530A1 were tested. The results were shown in Table 12.

TABLE 12

| Solid Form | MV (μm) | D10 (μm) | D50 (μm) | D90 (μm) |
|---|---|---|---|---|
| Form B | 3.12 | 1.20 | 2.73 | 5.49 |
| Form I | 136.1 | 24.97 | 100.5 | 297.4 |

MV: Average particle size by volume
D10: The D10 describes the diameter where 10% of the distribution has a smaller particle size.
D50: The D50 describes the diameter where 50% of the distribution has a smaller particle size, also called median size.
D90: The D90 describes the diameter where 90% of the distribution has a smaller particle size.

Figure 18:
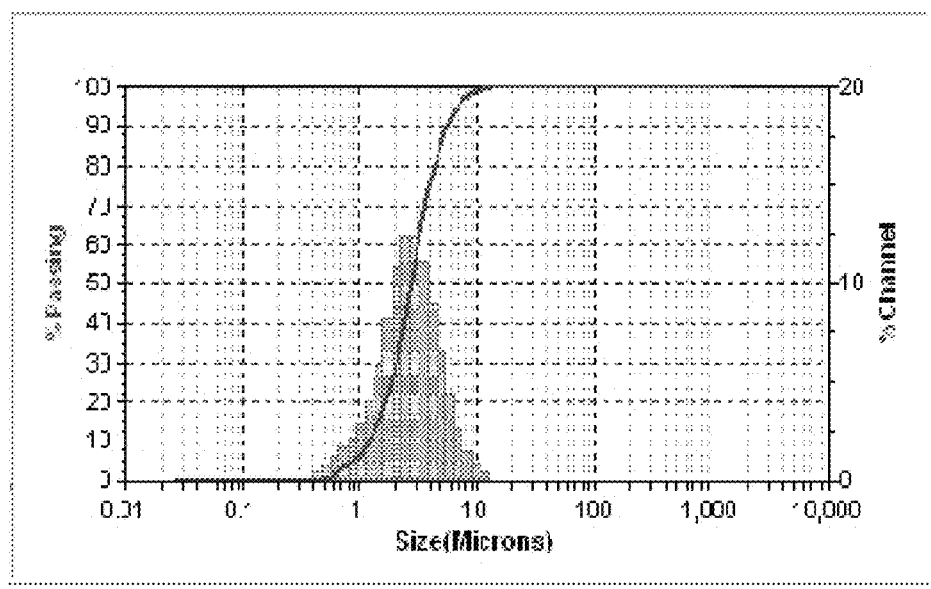
FIG. 18 shows a particle size distribution image of Form B.
Figure 19:
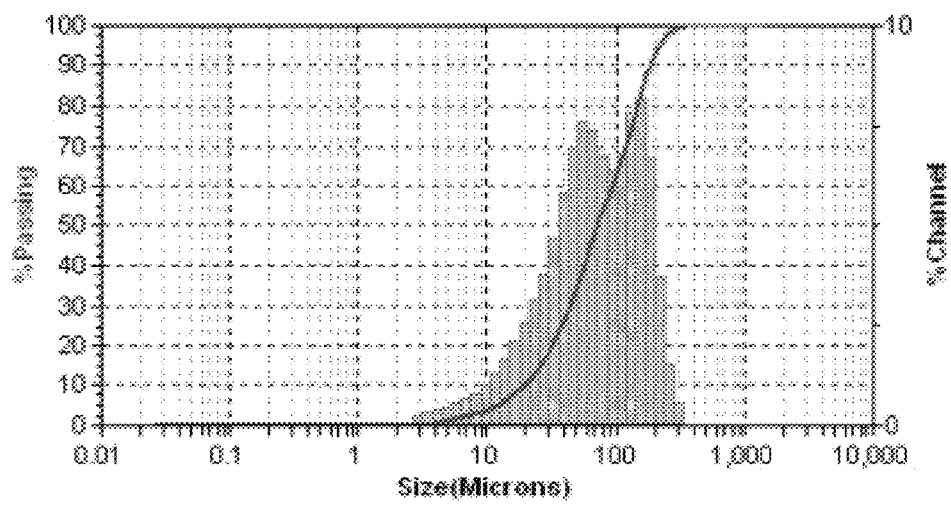
FIG. 19 shows a particle size distribution image of crystalline form I in WO2016120530A1.

The particle size distribution (PSD) pattern of Form B was shown in FIG. 18, and the particle size distribution (PSD) pattern of crystalline form I disclosed in WO2016120530A1 was shown in FIG. 19. It can be seen that the particle size of Form B has unimodal and normal distribution. The particle size has good uniformity and narrow distribution. While the particle size of crystalline form I shows a bimodal distribution with poor uniformity.

Different crystalline forms may exhibit different compressibility, bulk density, flowability, grinding stability, pressure stability and pulverization stability due to different particle properties, thus affecting the formulation process. For example, a narrower particle size distribution can improve the uniformity of the drug substance in the drug product, and reduce the variability in different batches, to get uniform dissolution. A smaller particle size can increase the specific surface area of the drug substance, and improve the dissolution rate of the drug, thereby facilitating drug absorption and further improving the bioavailability of the drug. In contrast, crystalline forms with bulk aggregation tend to cause residual solvents or other impurities. Moreover, in the formulation process, bulk crystalline powder cannot be uniformly dispersed, and is difficult to mix uniformly with the excipients, which is detrimental to formulation preparation.

Form B of the present disclosure shows regular shape. The uniform and small particle size is helpful to simplify the post-treatment of the formulation process, for example, less grinding can save cost and reduce the risk of crystallinity change and crystal transformation in grinding, thus improving the quality control of the drug. Additionally, narrower particle size distribution of Form B improves the uniformity of active pharmaceutical ingredients in drug products; smaller particle size distribution of Form B can increase the specific surface area of the drug substance, and improve the dissolution rate of the drug, thereby facilitating drug absorption and further improving bioavailability of the drug.

EXAMPLE 13: GRINDING STABILITY OF FORM C

Figure 20:
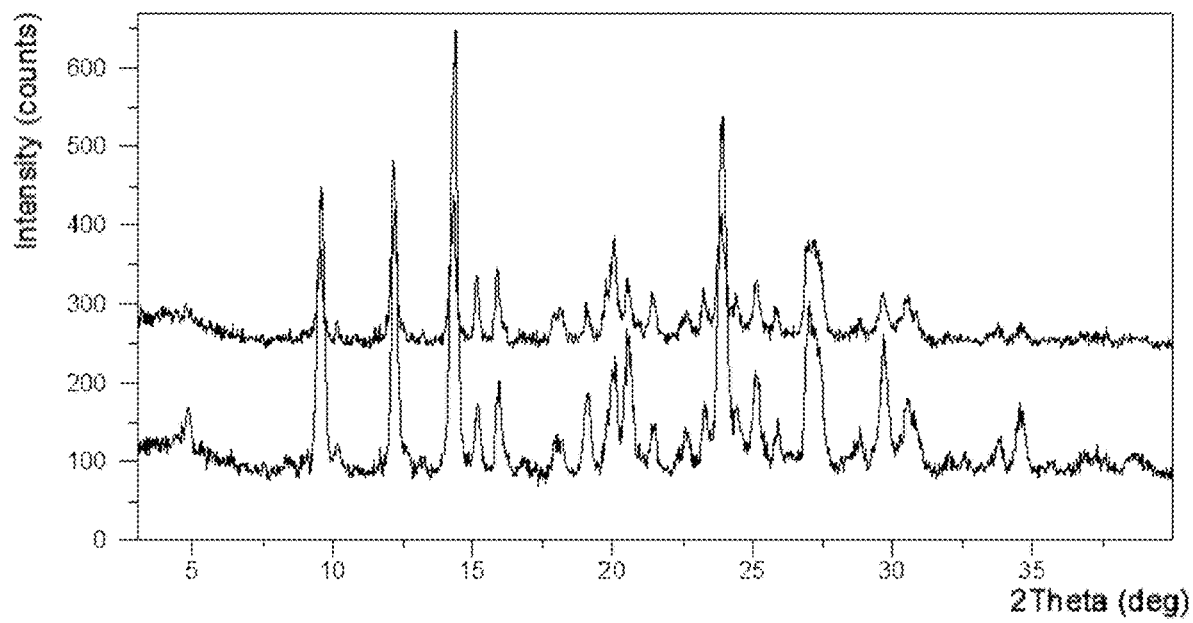
FIG. 20 shows an XRPD pattern overlay of Form C before and after grinding (top: XRPD pattern after grinding, bottom: XRPD pattern before grinding).
Figure 21:
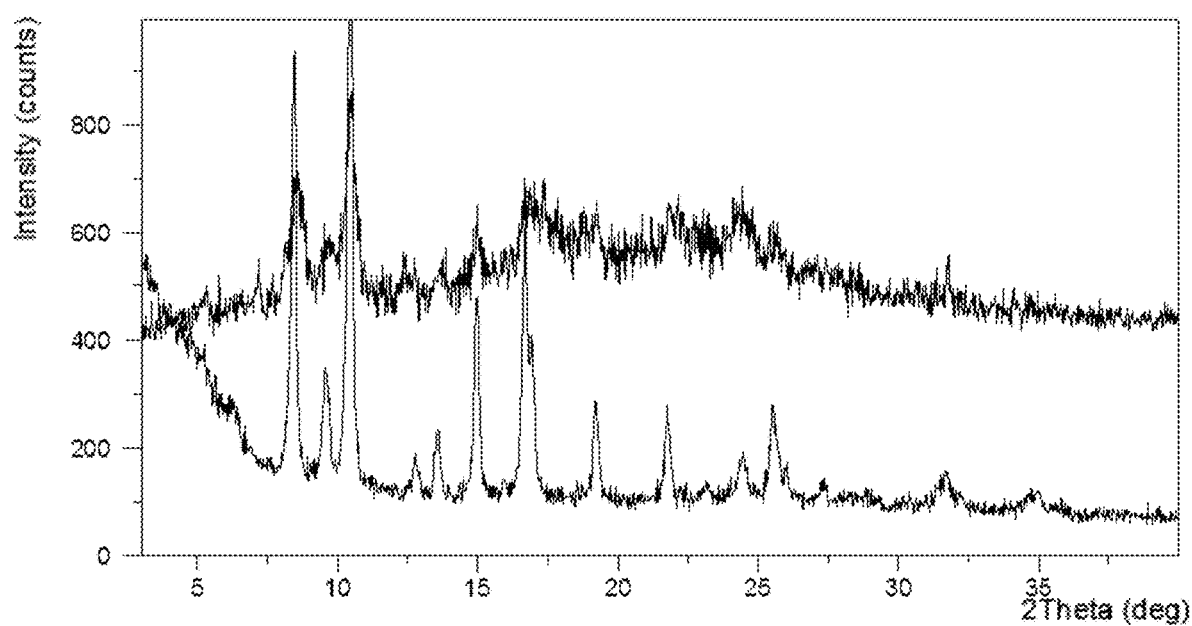
FIG. 21 shows an XRPD pattern overlay of crystalline form I in WO2016120530A1 before and after grinding (top: XRPD pattern after grinding, bottom: XRPD pattern before grinding).

About 20 mg of Form C in the present disclosure and crystalline form I disclosed in WO2016120530A1 were manually ground in a mortar for 5 minutes. XRPD tests of the samples before and after grinding were carried out. The XRPD patterns of Form C were shown in FIG. 20 (top: XRPD pattern after grinding, bottom: XRPD pattern before grinding), and the XRPD patterns of crystalline form I were shown in FIG. 21 (top: XRPD pattern after grinding, bottom: XRPD pattern before grinding). It can be seen from the Figures that Form C in the present disclosure remains good crystallinity after grinding, while the crystallinity of Form I decreased significantly, indicating better grinding stability of Form C in the present disclosure compared with that of crystalline form I disclosed in WO2016120530A1.

The above results indicate that Form C has a better mechanical stability and may provide more options in subsequent formulation processes. For example, Form C can be grounded by dry grinding method to get crystal with smaller particle size.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure

What is claimed is:

1. A crystalline form B of ODM-201 represented by formula (I), wherein the X-ray powder diffraction pattern shows characteristic peaks at 2theta values of 16.2°±0.2°, 9.0°±0.2° and 22.5°±0.2° using CuKα radiation Formula (I)

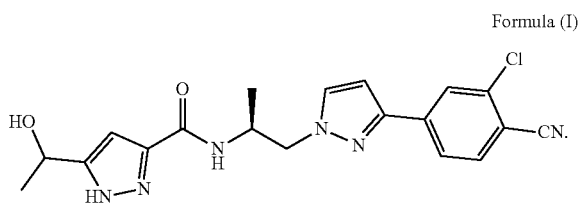 [SMILES: CC(O)c1cc(C(=O)N[C@@H](C)Cn2ccc(-c3ccc(C#N)c(Cl)c3)n2)n[nH]1]

2. The crystalline form B of ODM-201 according to claim 1, wherein the X-ray powder diffraction pattern shows one or two or three characteristic peaks at 2theta values of 24.7°±0.2°, 11.9°±0.2° and 18.1°±0.2° using CuKα radiation.

3. The crystalline form B of ODM-201 according to claim 1, wherein the X-ray powder diffraction pattern shows one or two or three characteristic peaks at 2theta values of 14.7°±0.2°, 23.5°±0.2° and 27.8°±0.2° using CuKα radiation.

4. A process for preparing crystalline form B of ODM-201 represented by formula (I) according to claim 1, wherein the process comprises:
  1) Dissolving ODM-201 into an alcohol or ketone or a mixed solvent of alcohol and ketone, then adding water dropwise as anti-solvent until solid precipitated; or
  2) Dissolving ODM-201 into mixed solvents of a halogenated hydrocarbon and an alcohol, or mixed solvents of an ether and water at room temperature, evaporating the clear solution at room temperature until solid precipitated.

5. The process for preparing crystalline form B of ODM-201 according to claim 4, wherein, said alcohol is methanol, ethanol or a mixture of methanol and ethanol; said halogenated hydrocarbon is chlorinated alkane; said ketone solvent is saturated aliphatic ketone; said ether is cyclic ether.

6. A crystalline form C of ODM-201 represented by formula (I),

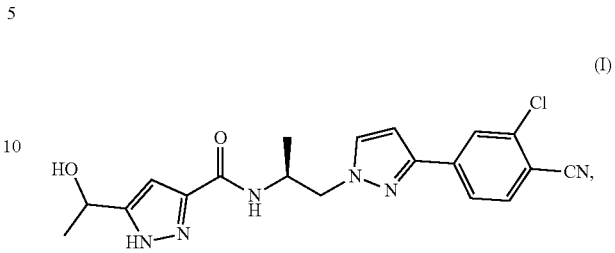

wherein the X-ray powder diffraction pattern shows characteristic peaks at 2theta values of 9.4°±0.2°, 14.1°±0.2° and 12.1°±0.2° using CuKα radiation.

7. The crystalline form C of ODM-201 according to claim 6, wherein the X-ray powder diffraction pattern shows one or two or three characteristic peaks at 2theta values of 15.1°±0.2°, 15.8°±0.2° and 19.9°±0.2° using CuKα radiation.

8. The crystalline form C of ODM-201 according to claim 6, wherein the X-ray powder diffraction pattern shows characteristic peak at 2theta value of 23.7°±0.2°.

9. A process for preparing crystalline form C of ODM-201 represented by formula (I) according to claim 6, wherein the process comprises: adding ODM-201 into a mixture system of acetic acid and other organic solvents at a certain volume ratio, and heating to a certain temperature followed by cooling and crystallization.

10. The process for preparing crystalline form C of ODM-201 according to claim 9, wherein, said other organic solvent is isopropanol or methyl tert-butyl ether; said heating temperature is 40-60° C.; said volume ratio is 2:1-1:2.

11. A pharmaceutical composition, wherein said pharmaceutical composition comprises a therapeutically effective amount of crystalline form B of ODM-201 according to claim 1, and pharmaceutically acceptable carriers, diluents or excipients.

12. A method of treating prostate cancer, comprising administering to a patient a therapeutically effective amount of crystalline form B of ODM-201 according to claim 1.

13. A pharmaceutical composition, wherein said pharmaceutical composition comprises a therapeutically effective amount of crystalline form C of ODM-201 according to claim 6, and pharmaceutically acceptable carriers, diluents or excipients.

14. A method of treating prostate cancer, comprising administering to a patient a therapeutically effective amount of crystalline form C of ODM-201 according to claim 6.

* * * * *